US012616400B2

(12) United States Patent
Ratcliff et al.

(10) Patent No.: US 12,616,400 B2
(45) Date of Patent: May 5, 2026

(54) SENSOR ARRAY SYSTEMS FOR REACTION MEASUREMENT BY ELECTRONIC GATE

(71) Applicant: ARIZONA BOARD OF REGENTS ON BEHALF OF THE UNIVERSITY OF ARIZONA, Tucson, AZ (US)

(72) Inventors: Erin L. Ratcliff, Tucson, AZ (US); Jonathan Harris, Tucson, AZ (US); Songyan Yu, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 405 days.

(21) Appl. No.: 18/312,955

(22) Filed: May 5, 2023

(65) Prior Publication Data

US 2023/0301564 A1      Sep. 28, 2023

Related U.S. Application Data

(63) Continuation-in-part of application No. PCT/US2022/079168, filed on Nov. 2, 2022, and a
(Continued)

(51) Int. Cl.
*A61B 5/1486* (2006.01)
*A61B 5/00* (2006.01)
(Continued)

(52) U.S. Cl.
CPC ........ *A61B 5/1486* (2013.01); *A61B 5/14546* (2013.01); *A61B 5/6801* (2013.01);
(Continued)

(58) Field of Classification Search
CPC . A61B 5/1486; A61B 5/14546; A61B 5/6801; A61B 5/7254; A61B 2562/046; G01N 27/3277; G01N 27/4145
See application file for complete search history.

(56) References Cited

U.S. PATENT DOCUMENTS

| | | | |
|---|---|---|---|
| 4,774,065 A | 9/1988 | Penzhorn et al. | |
| 6,638,482 B1 | 10/2003 | Ackley et al. | |

(Continued)

FOREIGN PATENT DOCUMENTS

| | | |
|---|---|---|
| CN | 106187981 A | 7/2016 |
| JP | 2006242900 A | 9/2006 |

(Continued)

OTHER PUBLICATIONS

Karbelkar, Amruta A., and Ariel L. Furst. "Electrochemical diagnostics for bacterial infectious diseases." ACS Infectious Diseases 6.7 (2020): 1567-1571.

(Continued)

*Primary Examiner* — Robert J Michaud

(74) *Attorney, Agent, or Firm* — NGUYEN TARBET IP LAW

(57)      ABSTRACT

The present invention is directed to devices for measuring reactions between a recognition element and a biological fluid (biomarker) to determine user well-being. The present invention features a sensor for analyzing a plurality of features of a reaction between an enzyme and a biomarker to measure a user's health. The sensor may comprise a substrate with an enzyme source and a drain. The enzyme source may comprise an enzyme path leading to a substrate surface to direct the enzyme to react with the biomarker to become a post-reaction mixture. The drain may comprise a drain path. The post-reaction mixture may travel from the substrate surface through the drain path to the drain. The sensor may further comprise an electronic gate disposed above the surface of the substrate for measuring the plurality of features. The sensor may be wearable on a skin surface of the user.

20 Claims, 2 Drawing Sheets

Related U.S. Application Data continuation-in-part of application No. PCT/US2021/058336, filed on Nov. 5, 2021.

(60) Provisional application No. 63/276,400, filed on Nov. 5, 2021, provisional application No. 63/110,211, filed on Nov. 5, 2020.

(51) Int. Cl.
| | |
|---|---|
| *A61B 5/145* | (2006.01) |
| *G01N 27/327* | (2006.01) |
| *G01N 27/414* | (2006.01) |

(52) U.S. Cl.
CPC ....... *A61B 5/7264* (2013.01); *G01N 27/3277* (2013.01); *G01N 27/4145* (2013.01); *A61B 2562/046* (2013.01)

(56) References Cited

U.S. PATENT DOCUMENTS

| | | | |
|---|---|---|---|
| 2007/0151942 A1 | 7/2007 | Dishough et al. | |
| 2013/0123596 A1 | 5/2013 | Kamath et al. | |
| 2019/0246959 A1* | 8/2019 | Ionescu .............. | A61B 10/0064 |
| 2025/0208117 A1* | 6/2025 | Howarth ................ | G01N 21/77 |

FOREIGN PATENT DOCUMENTS

| | | |
|---|---|---|
| JP | 2013050426 A | 3/2013 |
| WO | 2020077304 A9 | 4/2020 |

OTHER PUBLICATIONS

Lee et al. ""Cut and stick" rubbery ion gels as high capacitance gate dielectrics." Advanced Materials 24.32 (2012): 4457-4462.
Pappa et al. "Direct metabolite detection with an n-type accumulation mode organic electrochemical transistor." Science advances 4.6 (2018): eaat0911.
Rivnay et al. "Organic electrochemical transistors with maximum transconductance at zero gate bias." Advanced Materials 25.48 (2013): 7010-7014.
Macchia et al. "Ultra-sensitive protein detection with organic electrochemical transistors printed on plastic substrates." Flexible and Printed Electronics 3.3 (2018): 034002.
Thévenot et al. "Electrochemical biosensors: recommended definitions and classification." Analytical Letters 34.5 (2001): 635-659.
Fernandes et al. "Comparing label free electrochemical impedimetric and capacitive biosensing architectures." Biosensors and Bioelectronics 57 (2014): 96-102.
Braga et al. "Quantitative image analysis as a tool for Yarrowia lipolytica dimorphic growth evaluation in different culture media." Journal of Biotechnology 217 (2016): 22-30.
Harris, Jonathan. Fundamentals and Applications of Organic Electrochemical Transistors for Biosensing. Diss. The University of Arizona, 2021.
Aung, Hnin W., Susan A. Henry, and Larry P. Walker. "Revising the representation of fatty acid, glycerolipid, and glycerophospholipid metabolism in the consensus model of yeast metabolism." Industrial biotechnology 9.4 (2013): 215-228.
Chevy, F., L. Humbert, and C. Wolf. "Sterol profiling of amniotic fluid: a routine method for the detection of distal cholesterol synthesis deficit." Prenatal Diagnosis: Published in Affiliation With the International Society for Prenatal Diagnosis 25.11 (2005): 1000-1006.
Dowling et al. "Characterization of contractile proteins from skeletal muscle using gel-based top-down proteomics." Proteomes 7.2 (2019): 25.
Fountain et al. "Analysis of carbohydrates by ultraperformance liquid chromatography and mass spectrometry." TIC 9.e6 (2009): 100.

Menzella et al. "Using chemobiosynthesis and synthetic mini-polyketide synthases to produce pharmaceutical intermediates in *Escherichia coli*." Applied and Environmental Microbiology 76.15 (2010): 5221-5227.
Quick, Matthias, and Jonathan A. Javitch. "Monitoring the function of membrane transport proteins in detergent-solubilized form." Proceedings of the National Academy of Sciences 104.9 (2007): 3603-3608.
Tanaka, Fukuyo, Yukio Magariyama, and Akihiro Miyanoshita. "Volatile biomarkers for early-stage detection of insect-infested brown rice: Isopentenols and polysulfides." Food chemistry 303 (2020): 125381.
Li et al. "Extraction of bioethanol from fermented sweet sorghum bagasse by batch distillation." Korean Journal of Chemical Engineering 34 (2017): 127-132.
Hu et al. "Engineering Saccharomyces cerevisiae cells for production of fatty acid-derived biofuels and chemicals. Open Biol 9: 190049." (2019).
Callejón et al. "Recent developments in the analysis of musty odour compounds in water and wine: A review." Journal of Chromatography A 1428 (2016): 72-85.
Romano et al. "Growth and volatile compound production by Brettanomyces/Dekkera bruxellensis in red wine." Journal of Applied Microbiology 104.6 (2008): 1577-1585.
Villalonga et al. "Disposable electrochemical biosensors for Brettanomyces bruxellensis and total yeast content in wine based on core-shell magnetic nanoparticles." Sensors and Actuators B: Chemical 279 (2019): 15-21.
Borisova et al. "Disposable electrochemical immunosensor for Brettanomyces bruxellensis based on nanogold-reduced graphene oxide hybrid nanomaterial." Analytical and Bioanalytical Chemistry 409 (2017): 5667-5674.
Chen et al. "Detection of Saccharomyces cerevisiae immobilized on self-assembled monolayer (SAM) of alkanethiolate using electrochemical impedance spectroscopy." Analytica chimica acta 554.1-2 (2005): 52-59.
Bankar, Ashok V., Ameeta R. Kumar, and Smita S. Zinjarde. "Environmental and industrial applications of Yarrowia lipolytica." Applied microbiology and biotechnology 84 (2009): 847-865.
Beopoulos et al. "Yarrowia lipolytica as a model for bio-oil production." Progress in lipid research 48.6 (2009): 375-387.
Adrio, José L. "Oleaginous yeasts: promising platforms for the production of oleochemicals and biofuels." Biotechnology and bioengineering 114.9 (2017): 1915-1920.
Beopoulos et al. "Control of lipid accumulation in the yeast *Yarrowia lipolytica*." Applied and environmental microbiology 74.24 (2008): 7779-7789.
Worland et al. "Analysis of Yarrowia lipolytica growth, catabolismand terpenoid biosynthesis during utilization of lipid- derived feedstock." Metabolic Engineering Communications 11 (2020): e00130.
Abraham et al. "2013 Index IEEE Reviews in Biomedical Engineering vol. 6." Biosensors 17: 18.
Asphahani, Fareid, and Miqin Zhang. "Cellular impedance biosensors for drug screening and toxin detection." Analyst 132.9 (2007): 835-841.
Sadeghi, S. J., Gianfranco Gilardi, and A. E. G. Cass. "Mediated electrochemistry of peroxidases—effects of variations in protein and mediator structures." Biosensors and Bioelectronics 12.12 (1997): 1191-1198.
Karadag et al. "Modified gold surfaces by 6-(ferrocenyl) hexanethiol/dendrimer/gold nanoparticles as a platform for the mediated biosensing applications." Materials Science and Engineering: C 33.2 (2013): 634-640.
Brothers et al. "Impact of self-assembled monolayer design and electrochemical factors on impedance-based biosensing." Sensors 20.8 (2020): 2246.
Ye, Shen, Yukari Sato, and Kohei Uosaki. "Redox-induced orientation change of a self-assembled monolayer of 11-ferrocenyl-1-undecanethiol on a gold electrode studied by in situ FT-IRRAS." Langmuir 13.12 (1997): 3157-3161.
Li et al. "Impedance based detection of pathogenic *E. coli* O157: H7 using a ferrocene-antimicrobial peptide modified biosensor." Biosensors and Bioelectronics 58 (2014): 193-199.

(56) References Cited

OTHER PUBLICATIONS

Bernards et al. "Enzymatic sensing with organic electrochemical transistors." Journal of Materials chemistry 18.1 (2008): 116-120.

He et al. "Detection of bacteria with organic electrochemical transistors." Journal of Materials Chemistry 22.41 (2012): 22072-22076.

Rivnay et al. "Organic electrochemical transistors for cell-based impedance sensing." Applied Physics Letters 106.4 (2015): 8_1.

Berto et al. "Label free urea biosensor based on organic electrochemical transistors." Flexible and Printed Electronics 3.2 (2018): 024001.

Stern et al. "Importance of the Debye screening length on nanowire field effect transistor sensors." Nano letters 7.11 (2007): 3405-3409.

Bernards, Daniel A., and George G. Malliaras. "Steady-state and transient behavior of organic electrochemical transistors." Advanced Functional Materials 17.17 (2007): 3538-3544.

Rivnay et al. "Organic electrochemical transistors." Nature Reviews Materials 3.2 (2018): 1-14.

Khodagholy et al. "High transconductance organic electrochemical transistors." Nature communications 4.1 (2013): 2133.

Mabeck et al. "Microfluidic gating of an organic electrochemical transistor." Applied Physics Letters 87.1 (2005): 013503.

Harris, Jonathan K., and Erin L. Ratcliff. "Ion diffusion coefficients in poly (3-alkylthiophenes) for energy conversion and biosensing: role of side-chain length and microstructure." Journal of Materials Chemistry C 8.38 (2020): 13319-13327.

Harris, Jonathan K., Bharati Neelamraju, and Erin L. Ratcliff. "Intersystem Subpopulation Charge Transfer and Conformational Relaxation Preceding in Situ Conductivity in Electrochemically Doped Poly (3-Hexylthiophene) Electrodes." Chemistry of Materials 31.17 (2019): 6870-6879.

Minamiki et al. "Accurate and reproducible detection of proteins in water using an extended-gate type organic transistor biosensor." Applied Physics Letters 104.24 (2014): 243703.

Hintz et al. "Photodegradation of P3HT—a systematic study of environmental factors." Chemistry of Materials 23.2 (2011): 145-154.

Parnell et al. "Physical mechanisms responsible for the water-induced degradation of PC61BM P3HT photovoltaic thin films." Journal of Polymer Science Part B: Polymer Physics 54.2 (2016): 141-146.

White, Scott P., Kevin D. Dorfman, and C. Daniel Frisbie. "Label-free DNA sensing platform with low-voltage electrolyte-gated transistors." Analytical chemistry 87.3 (2015): 1861-1866.

Lin, Fuding, and Mark C. Lonergan. "Gate electrode processes in an electrolyte-gated transistor: Non-Faradaically versus Faradaically coupled conductivity modulation of a polyacetylene ionomer." Applied physics letters 88.13 (2006): 133507.

Tarabella et al. "Effect of the gate electrode on the response of organic electrochemical transistors." Applied Physics Letters 97.12 (2010): 205.

Jamasb et al. "Accurate continuous monitoring using ISFET-based biosensors based on characterization and modelingof drift and low frequency noise." Proceedings of the 20th Annual International Conference of the IEEE Engineering in Medicine and Biology Society. vol. 20 Biomedical Engineering Towards the Year 2000 and Beyond (Cat. No. 98CH36286). vol. 6. IEEE, 1998.

Krishnamurthy, Vikram, Sahar Moradi Monfared, and Bruce Cornell. "Ion channel biosensors—Part II: Dynamic modeling, analysis, and statistical signal processing." IEEE Transactions on Nanotechnology 9.3 (2010): 313-321.

White, Scott P., C. Daniel Frisbie, and Kevin D. Dorfman. "Detection and sourcing of gluten in grain with multiple floating-gate transistor biosensors." ACS sensors 3.2 (2018): 395-402.

White, Scott P., Kevin D. Dorfman, and C. Daniel Frisbie. "Operating and sensing mechanism of electrolyte-gated transistors with floating gates: Building a platform for amplified biodetection." The Journal of Physical Chemistry C 120.1 (2016): 108-117.

Thomas et al. "Interfacial charge contributions to chemical sensing by electrolyte-gated transistors with floating gates." The journal of physical chemistry letters 9.6 (2018): 1335-1339.

Myszka, David G. "Improving biosensor analysis." Journal of molecular recognition 12.5 (1999): 279-284.

Park et al. "Functional characterization of extracellular chitinase encoded by the YI CTS1 gene in a dimorphic yeast Yarrowia lipolytica." Journal of Microbiology 52 (2014): 284-291.

Dichiarante et al. "A short-chain multibranched perfluoroalkyl thiol for more sustainable hydrophobic coatings." Acs Sustainable Chemistry & Engineering 6.8 (2018): 9734-9743.

Rickert et al. "A 'mixed'self-assembled monolayer for an impedimetric immunosensor." Biosensors and Bioelectronics 11.8 (1996): 757-768.

Bueno, Paulo R., Gustavo T. Feliciano, and Jason J. Davis. "Capacitance spectroscopy and density functional theory." Physical Chemistry Chemical Physics 17.14 (2015): 9375-9382.

Brug et al. "The analysis of electrode impedances complicated by the presence of a constant phase element." Journal of electroanalytical chemistry and interfacial electrochemistry 176.1-2 (1984): 275-295.

Protsailo, Lesia V., and W. Ronald Fawcett. "Studies of electron transfer through self-assembled monolayers using impedance spectroscopy." Electrochimica Acta 45.21 (2000): 3497-3505.

White et al. "Rapid, selective, label-free aptameric capture and detection of ricin in potable liquids using a printed floating gate transistor." ACS Sensors 1.10 (2016): 1213-1216.

Castiello et al. "Interfacial capacitance immunosensing using interdigitated electrodes: the effect of insulation/immobilization chemistry." Physical Chemistry Chemical Physics 21.28 (2019): 15787-15797.

* cited by examiner

SENSOR ARRAY SYSTEMS FOR REACTION MEASUREMENT BY ELECTRONIC GATE

CROSS-REFERENCES TO RELATED APPLICATIONS

This application is a Continuation-In-Part and claims benefit of PCT Application No. PCT/US2021/058336 filed Nov. 5, 2021, which claims benefit of U.S. Provisional Patent Application No. 63/110,211 filed Nov. 5, 2020, the specifications of which are incorporated herein in their entirety by reference.

This application is also a Continuation-In-Part and claims benefit of PCT Application No. PCT/US2022/079168 filed Nov. 2, 2022, which claims benefit of U.S. Provisional Patent Application No. 63/276,400 filed Nov. 5, 2021, the specifications of which are incorporated herein in their entirety by reference.

FIELD OF THE INVENTION

The present invention is directed to methods, sensor systems, and devices for measuring reactions between a recognition element and a reactant such as but not limited to a biological fluid (biomarker).

BACKGROUND OF THE INVENTION

Organic electrochemical transistors (OECTs) have garnered considerable interest for sensing and bioelectronics applications, as the device architecture enables simple electrical readout, convenient fabrication, fast manufacturing on flexible substrates, and straightforward miniaturization for lab-on-a-chip applications with versatile geometries. Of particular note, OECTs exhibit a hybrid electrical-ionic conduction mechanism, where electrochemical doping/de-doping of the channel yields a significant modulation of conductivity at low operating voltages (<1 V). This effect enables very low levels of detection of biological materials through signal amplification. Given the exciting attributes of OECTs as sensors, several models have been developed to understand the operation of the OECT. One mode is the capacitive mode, whereby the gate electrode and channel are treated as capacitors in series. The device response is highly dependent on electrolyte potential, where capacitances of the semiconductor channel can change from 1-10 µF/cm2 (double-layer-like) to >103 µF/cm3 (volumetric) over 100 mV. A second mode, termed the faradaic mode, is achieved via electron transfer (i.e., redox reactions) at the gate electrode. This mode enables the majority of the electric field to drop across the polymer channel, yielding higher amplifications than in a non-faradaic (capacitive) mode.

The present invention is directed to OECTs operated in the faradaic mode. For sensing applications including wearables, microfluidics, and/or implantable devices, one must balance size, target analyte concentration, biocompatibility, fabrication, and the cost of the net sensor design. Thus, a better performing OECT (higher transconductance) may not necessarily translate to higher sensitivity. For sensors, key advantages of the faradaic mode OECT are directly connected to ultralow level analyte detection, whereby reduction in device size may have the following advantages: opportunities to approach single-molecule/entity detection, inherently less power due to less current draw from smaller electrodes, enhanced mass transport effects, reduction in cost associated with bio-recognition elements and/or microfluidics, and translation to multiplexing and/or small fluid volumes (nL to fL). Demonstrations of faradaic mode OECT sensors to date are quantification of redox-active biomarkers H2O2, glucose, and dopamine. More recently, the introduction of redox probes/catalysis at OECT gate electrodes facilitates the detection of more complex biologically-relevant species. A similar approach combining redox-active molecules with chemically selective bio-recognition elements in a mixed monolayer at an electrode is gaining traction in electrochemical impedance-based sensing.

The present invention describes how the redox behavior at the gate can be used to lower OECT operating power, specifically its onset voltage and maximum transconductance, with the outcome of combining redox moieties for high amplification in the faradaic mode with chemical selectivity of a surface-confined bio-recognition element. Since the electrochemical doping process of the polymer channel is coupled by the reaction at the gate in the faradaic mode, the effective density of states (DOS) overlaps between the two processes (as a function of electrolyte potential) plays a crucial role in determining OECT characteristics. The present invention describes implementing two common p-type polymers, poly(3-hexylthiophene) (P3HT) and poly[2-5-bis(3-dode-cylthiophen-2-yl)thieno[3, 2-b ]thiophene)] (PBTTT-C12), and a set of representative redox molecules with varying redox potentials. Aligning the oxidation potential of the polymer with the reduction potential of the electrolyte oxidant, the gate voltage can be successfully minimized at maximum transconductance, toward realization of a self-driven or self-powered gate device.

The present invention implements a Marcus—Gerischer perspective for electrochemical events at both the gate and semiconductor channel. This electrochemical perspective is selected as it enables a direct energy connection between the density of electrochemically active states of the semiconductor channel with respect to the DOS of the electrolyte and the gate electrode, all independently measured parameters. This gate material-agnostic approach allows the present invention to account for not only a work function or relative Fermi level of electrochemical interfaces but also differences due to (electro)chemical potentials, dipoles, charge transfer events, free carrier distributions, solvent and/or supporting electrolyte effects, and semiconductor channel geometry, parameters not fully accounted for in existing OECT models. Additionally, by lowering the necessary gate voltage, the stability of sensors could be enhanced.

Many bio-recognition elements (e.g.,i.e., bilayer membranes, antibodies/aptamers, cells, etc.) immobilized on the gate electrode tend to degrade due to prolonged application of high voltage; one predominant mechanism is irreversible faradaic stripping reactions. More broadly, low or self-powered OECT devices could eliminate requisite circuits with two power supplies, which are challenging when the lab-on-chip platform or wearable bioelectronics integrated with numerous fluidic, electronic, and mechanical components are taken into consideration.

BRIEF SUMMARY OF THE INVENTION

It is an objective of the present invention to provide devices and methods that allow for measuring reactions between a first reactant and a second reactant, such as but not limited to reactions between an enzyme and a biomarker, to determine one or more properties pertaining to the source of the second reactant, e.g., a user's well-being, soil health, yeast production.

Embodiments of the present invention can be freely combined with each other if they are not mutually exclusive.

The present invention is applicable to the field of sweat-based biomarker research, among other applications such as but not limited to environmental health measurement, food and beverage analysis, and yeast production. An example of an application of this is in the capture of "in the moment" spikes in the stress response for military, first responders, and others working under peaking stress conditions. The non-electronic, hands-free sweat collection device of the present invention yields standardized sweat samples collection, directly addressing an immediate need and will find interest from a wide range of applications including medical, first responders, athletes, researchers, device developers, etc. Second, the biochemistry of sweat is under-characterized and common biomedical challenges including non-specific adsorption and enzymatic degradation of peptides continue to be less considered, particularly in the context of printable electronic devices. The present invention features a universal, printable transistor sensing platform, which will easily extend research beyond neuropeptides to facilitate future development of rapid, label-free, highly sensitive all-printed sensor arrays and disposable diagnostic devices. This may enable both bio-recognition and electrochemical detection strategies with low limits of detection ($\mu M$ to pM concentrations) in small volumes ($\mu L$ to nL) in real-time (<1 minute), depending on architecture and detection schemes.

The present invention features a sensor for analyzing one or more features of a reaction between a first reactant and a second reactant. The sensor may comprise a substrate with a reactant source and a reactant path leading to a surface of the substrate such that the first reactant travels from the source through the path to the surface to react with the second reactant to become a post-reaction mixture on the surface of the substrate. The substrate may further comprise a drain and a drain path such that the post-reaction mixture travels from the surface of the substrate through the drain path to the drain. The sensor may further comprise an electronic gate in fluid communication with the post-reaction mixture for measuring the one or more features of the reaction between the first reactant and the second reactant. A feature analyzed by the sensor may be a rate constant of the reaction, a concentration of the first reactant in the post-reaction mixture, a concentration of the second reactant in the post-reaction mixture, and/or an amount of energy produced by the reaction.

The present invention features a system for analyzing two or more sets of features of reactions between a plurality of first reactants and a second reactant. The system may comprise two or more sensors, each sensor analyzing a different reaction between a first reactant and the second reactant. Each sensor may comprise a substrate with a reactant source and a reactant path leading to a surface of the substrate such that the first reactant travels from the source through the path to the surface to react with the second reactant to become a post-reaction mixture on the surface of the substrate. The substrate may further comprise a drain and a drain path such that the post-reaction mixture travels from the surface of the substrate through the drain path to the drain. The sensor may further comprise an electronic gate in fluid communication with the post-reaction mixture for measuring the one or more features of the reaction between the first reactant and the second reactant. A feature analyzed by the sensor may be a rate constant of the reaction, a concentration of the first reactant in the post-reaction mixture, a concentration of the second reactant in the post-reaction mixture, and/or an amount of energy produced by the reaction. The system may further comprise a computing device for accepting the two or more feature sets from the two or more sensors and analyzing the two or more feature sets. The array of sensors may be capable of tracking multiple reactions over different times and locations to determine various additional properties of the second reactant.

The present invention features a method for analyzing one or more features of a reaction between a first reactant and a second reactant. The method may comprise providing a sensor having a substrate with a reactant source and a reactant path leading to a surface of the substrate such that the first reactant travels from the source through the path to the surface to react with the second reactant to become a post-reaction mixture on the surface of the substrate. The substrate may further comprise a drain and a drain path such that the post-reaction mixture travels from the surface of the substrate through the drain path to the drain. The sensor may further comprise an electronic gate in fluid communication with the post-reaction mixture for measuring the one or more features of the reaction between the first reactant and the second reactant. A feature analyzed by the sensor may be a rate constant of the reaction, a concentration of the first reactant in the post-reaction mixture, a concentration of the second reactant in the post-reaction mixture, and/or an amount of energy produced by the reaction. The method may further comprise applying the second reactant to the sensor and analyzing a readout from the electronic gate upon detecting the reaction between the first reactant and the second reactant.

The second reactant may be derived from a biological fluid from an animal, plant, or environment, or an artificial fluid for consumption or medical purposes and the surface may be accessible to the second reactant. Analyzing the one or more features may allow the sensor to measure physiological parameters based on fluids produced by a human, yeast production in biofuel, or environmental parameters in a natural environment. The first reactant may comprise an antibody, an aptamer, an ion gel, a protein, a peptide, a neurotransmitter, a neuropeptide, a gas molecule, a carbohydrate, a lipid, or a combination thereof, and the second reactant may comprise an antibody, an aptamer, an ion gel, a protein, a peptide, a neurotransmitter, a neuropeptide, a gas molecule, a carbohydrate, a lipid, or a combination thereof. The sensor may further comprise a pump for directing the first reactant from the reactant source through the reactant path to the surface of the substrate. The reactant path may comprise a plurality of capillaries such that the first reactant may be directed through the reactant path by a wicking action. The plurality of capillaries may comprise a plurality of microfluidic capillaries.

The computing device may comprise a processor capable of executing computer-readable instructions and a memory component comprising a plurality of computer-readable instructions for implementing a machine learning algorithm for analyzing the one or more features. The array of sensors may be capable of measuring one or more array features selected from a group consisting of spatial distribution, distribution of rate constants, and a variety of analytes. The electronic gate may be disposed above, lateral to, behind, or in front of the surface of the substrate. The sensor may further comprise an attachment component allowing the sensor to attach to a surface or tissue. The surface or tissue may be an animal surface, an animal tissue, a synthetic surface, or a natural surface. The natural surface may be soil, a plant, or any surface that may be found in nature.

The sensor may further comprise an electrolyte disposed between the electronic gate and the substrate. The electrolyte may comprise a redox-based modifier having a reduction (or oxidation) potential that may be energetically equivalent to the substrate. A surface of the electronic gate may comprise an oxidation (or reduction) element. The substrate may comprise a solid-state printable material. The sensor may further comprise an interacting channel comprising a first control gate electrode and a first solid-state analyte disposed in a first biofluid for providing a charge transfer to the electronic gate. The sensor may further comprise a reference channel comprising a second control gate electrode and a second solid-state analyte identical to the first solid-state analyte disposed in a second biofluid identical to the first biofluid to allow for drift correction of an output of the sensor. The substrate may further comprise of semi-conducting polymers, such as poly(3-hexylthiophene) (P3HT) and poly[2-5-bis(3-dode-cylthiophen-2-yl)thieno[3,2-b]thiophene)] (PBTTT-C12). The sensor may implement a Marcus-Gerischer perspective for reactions at the electronic gate. The sensor may be low powered or self-powered.

The present invention also features an all-printed array of organic electrochemical transistors (OECTs). Each of these transistors could be a single-gate and/or multi-gate configuration. In some embodiments, the present invention may implement dual floating gate architectures. The gates of the present invention may be disposed laterally to or stacked on top of a substrate. In some embodiments, there are two channels in separate "electrolytes" which can be a solution or solid-state and the two floating gates (FG) are in electrical contact with one another. This electrical contact can be a quite large distance—feet to meters apart if necessary.

One of the unique and inventive technical features of the present invention is the implementation of an electronic gate for measuring a plurality of features of a reaction between an enzyme and a biomarker. Without wishing to limit the invention to any theory or mechanism, it is believed that the technical feature of the present invention advantageously provides for compact and efficient determination of a user's health using biomarker measurements. None of the presently known prior references or work has the unique inventive technical feature of the present invention.

Another one of the unique and inventive technical features of the present invention is redox-based modifiers implemented in the electrolyte of the OECT, whereby the redox moiety has a reduction (or oxidation) potential that is energetically equivalent to the oxidation (or reduction) potential of the conductive polymer. This electrolyte can be a solution or a solid-state electrolyte. Without wishing to limit the invention to any theory or mechanism, it is believed that the technical feature of the present invention advantageously provides for the creation of multiple stacks of electrolyte to prevent the reduction molecule from interacting with the polymer. None of the presently known prior references or work has the unique inventive technical feature of the present invention.

Another one of the unique and inventive technical features of the present invention is the implementation of an oxidation (or reduction) element to the surface of a floating gate or multiple floating gates. Without wishing to limit the invention to any theory or mechanism, it is believed that the technical feature of the present invention advantageously provides for a greater amplification response over impedance-based sensors, with lower power and simplified electronics. If the oxidation (or reduction) potential of a first floating gate is matched to the reduction (oxidation) potential of another floating gate and the oxidation (reduction)

potential of the substrate, this is the lowest power response. None of the presently known prior references or work has the unique inventive technical feature of the present invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which.

DETAILED DESCRIPTION OF THE INVENTION

Figure 1:
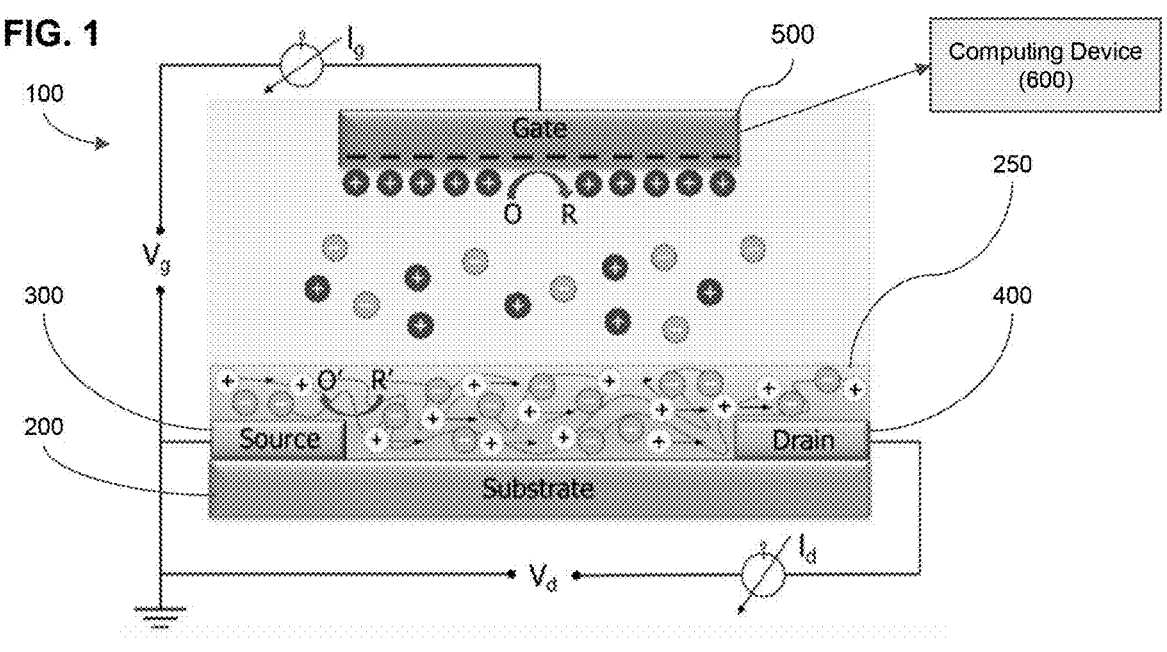
FIG. 1 shows a diagram of a sensor of the present invention for measuring reactions between an enzyme and a biomarker.
Figure 4:
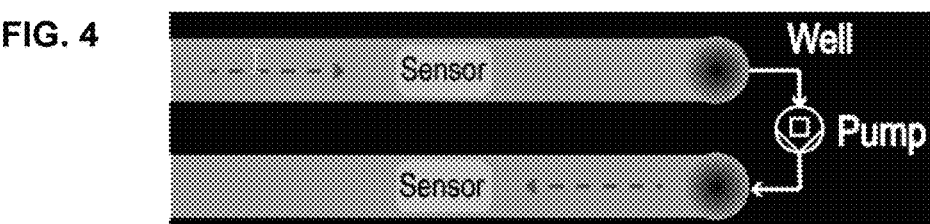
FIG. 4 shows a diagram of a sensor of the present invention comprising a pump.
Figure 5:
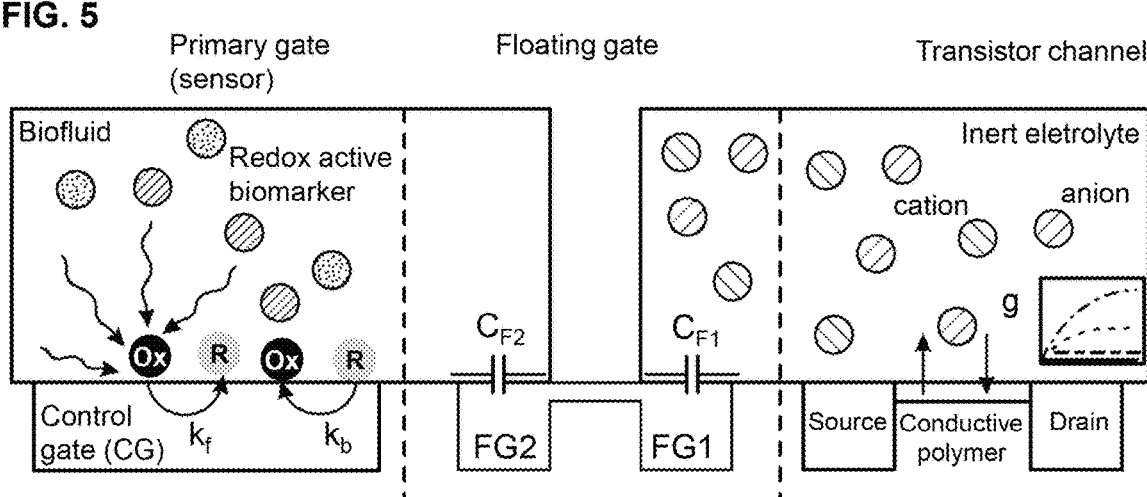
FIG. 5 shows a diagram of the sensor platform of the present invention comprising a primary gate electrode and a floating gate electrode interfaced with one electrolyte (i.e. biofluid) and a transistor channel, and a second floating gate interfaced with a second electrolyte.

Referring now to FIG. 1, the present invention features a sensor (100) for analyzing a plurality of features of a reaction between an enzyme and a biomarker to measure a user's health. In some embodiments, the sensor (100) may comprise a substrate (200). The substrate (200) may comprise an enzyme source (300). The enzyme source (300) may comprise an enzyme path leading to a surface (250) of the substrate (200). The enzyme contained in the enzyme source (300) may travel through the enzyme path to react with the biomarker to become a post-reaction mixture on the surface (250) of the substrate (200). The enzyme source (300) may comprise a well, as seen in FIG. 5. The substrate (200) may further comprise a drain (400). The drain (400) may comprise a drain path. The post-reaction mixture may travel from the surface (250) of the substrate (200) through the drain path to the drain (400). The reaction may take place in a channel on the surface (250) of the substrate (200), as seen in FIG. 4. The sensor (100) may further comprise an electronic gate (500) disposed above the surface (250) of the substrate (200) for measuring the plurality of features of the reaction between the enzyme and the biomarker. The biomarker may comprise a bodily fluid produced by an animal. The animal may be a human.

The plurality of features may comprise a rate constant of the reaction, a concentration of enzyme in the post-reaction mixture, and an amount of energy produced by the reaction.

The sensor (100) may be wearable on a skin surface of the user and may attach to the skin surface of the user by an adhesive, a strap, or any apparatus that allows the sensor (100) to constantly contact the skin surface. In some embodiments, the enzyme may comprise antibodies, aptamer, ion gel, or a combination thereof. In some embodiments, the surface (250) of the substrate (200) may comprise a film, nanoparticles, or a combination thereof. In some embodiments, the electronic gate (500) may comprise gold and the substrate (200) may comprise a conductive polymer. In some embodiments, the biomarker may comprise sweat. In some embodiments, the sensor (100) may further comprise a pump for directing the enzyme from the enzyme source (300) through the enzyme path to the surface (250) of the substrate (200).

Figure 2:
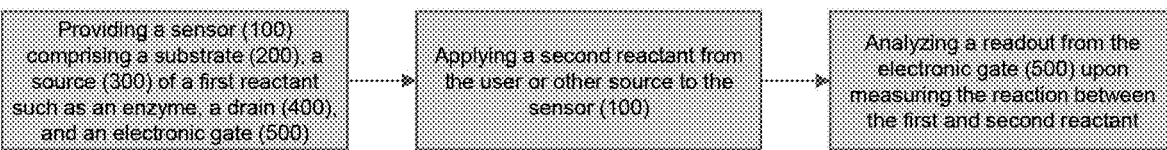
FIG. 2 shows a flow chart of a method of the present invention for measuring reactions between an enzyme and a biomarker.
Figure 3:
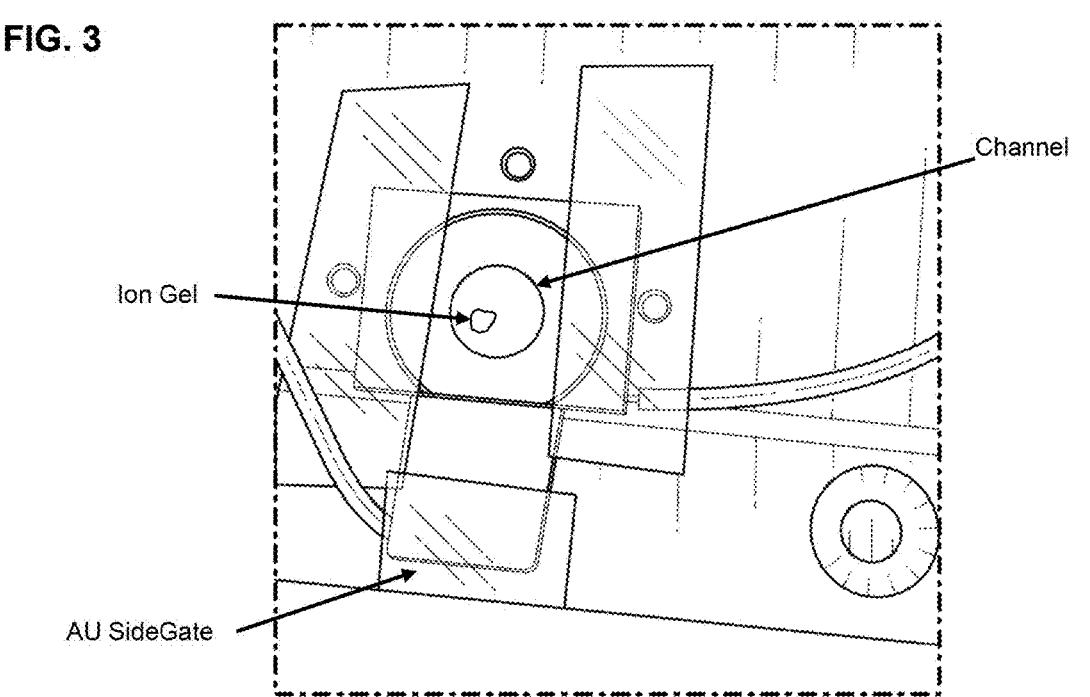
FIG. 3 shows a photograph of an embodiment of a sensor of the present invention.

Referring now to FIG. 2, the present invention features a method for analyzing a plurality of features of a reaction between an enzyme and a biomarker to measure a user's health. In some embodiments, the method may comprise providing a sensor (100). In some embodiments, the sensor (100) may comprise a substrate (200). The substrate (200) may comprise an enzyme source (300). The enzyme source (300) may comprise an enzyme path leading to a surface (250) of the substrate (200). The enzyme source (300) may comprise a well, as seen in FIG. 5. The enzyme contained in the enzyme source (300) may travel through the enzyme path to react with the biomarker to become a post-reaction mixture on the surface (250) of the substrate (200). The substrate (200) may further comprise a drain (400). The drain (400) may comprise a drain path. The post-reaction mixture may travel from the surface (250) of the substrate (200) through the drain path to the drain (400). The reaction may take place in a channel on the surface (250) of the substrate (200), as seen in FIG. 4. The sensor (100) may further comprise an electronic gate (500) disposed above the surface (250) of the substrate (200) for measuring the plurality of features of the reaction between the enzyme and the biomarker. The biomarker may comprise a bodily fluid produced by the user. The plurality of features may comprise a rate constant of the reaction, a concentration of enzyme in the post-reaction mixture, and an amount of energy produced by the reaction. The method may further comprise applying the biomarker from the user to the sensor (100). The method may further comprise using a computing device (600) to analyze a readout from the electronic gate (500) upon detecting the reaction between the enzyme and the biomarker.

The sensor (100) may be wearable on a skin surface of the user and may attach to the skin surface of the user by an adhesive, a strap, or any apparatus that allows the sensor (100) to constantly contact the skin surface. In some embodiments, the enzyme may comprise antibodies, aptamer, ion gel, or a combination thereof. In some embodiments, the surface (250) of the substrate (200) may comprise a film, nanoparticles, or a combination thereof. In some embodiments, the electronic gate (500) may comprise gold and the substrate (200) may comprise a conductive polymer. In some embodiments, the biomarker may comprise sweat. In some embodiments, the sensor (100) may further comprise a pump for directing the enzyme from the enzyme source (300) through the enzyme path to the surface (250) of the substrate (200).

Reactions may occur at the gate electrode (500) or the semiconductor channel, both of which can alter the voltage-dependent conduction properties of the semiconductor. Mechanisms include capacitive through interaction with ions at surfaces of the gate (500) or semiconductor, changes in capacitance due to the binding of biomarkers with adsorbed antibodies, aptamers, etc., or through electron transfer events with redox-active species which may include enzymes, biomarkers, or water and water dissociation products (protons, hydroxyls, peroxides, hydrogen, oxygen).

The present invention can include applications for wearables, specifically, sweat sensors and/or implantables as well as be considered as a diagnostic tool and research aid for biomarker/enzyme interactions. The sensor may be completely printable by a 3D printing platform for manufacturing efficiency.

The present invention may incorporate a vacuum to act as a driving force for sweat collection which may be important to achieve 1 mL/min of sweat collection for wearable devices on the skin because the collected amount of sweat will be dependent on both the sweat rate and available skin surface area.

Referring now to FIG. 5, the present invention features a sensor device implementing a side floating gate architecture, whereby the source-drain transducer channel is chemically isolated from the molecular capture. A printable ionic liquid and/or solid-state electrolyte (gel, polyelectrolyte, etc) may be used to maintain ionic contact. Briefly, the device may comprise three key elements: i) a primary gate electrode within a microfluidic channel containing the biofluid. A chemical reaction at the gate (primary or floating gate) electrode may be responsible for inducing a change in conductivity in the channel. Two key mechanisms may be used to detect a biomarker: electrochemically undergoing electron transfer to a redox-active biomarker (as shown) or modification of the metal surface with bio-recognition elements, such as antibodies for selective capture; ii) a transistor channel interfaced with an ionic liquid that acts as the amplifier by changing in conductivity; and iii) a floating gate (FG) electrode interfaced on one side with an inert electrolyte (such as an ionic liquid) and the other side with the biofluid.

Figure 6:
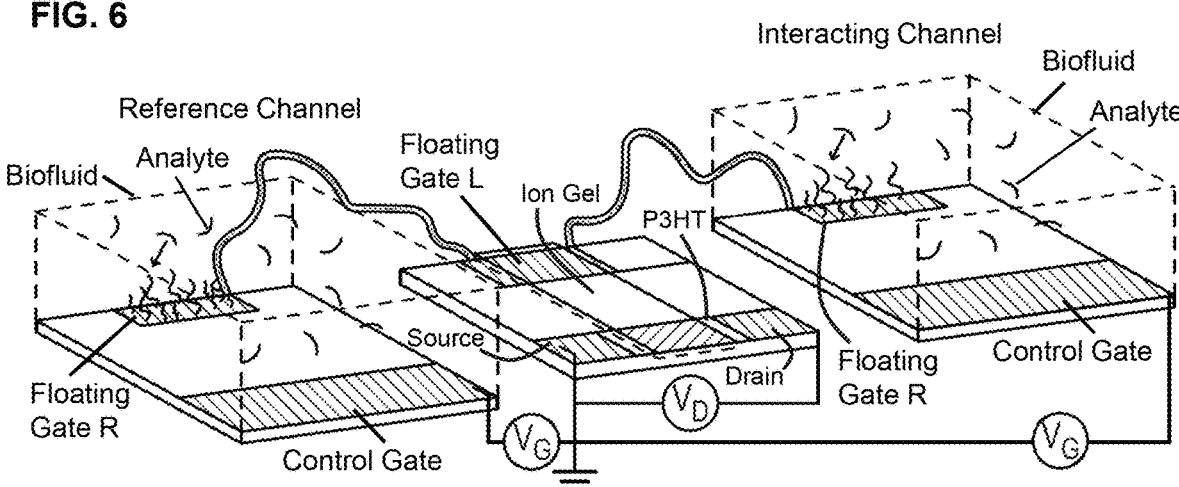
FIG. 6 shows a diagram of the sensor platform of the present invention comprising a floating gate having two arms, an interacting channel and a reference channel.

Referring now to FIG. 6, the present invention features a sensor device for analyzing a plurality of features of a reaction between an enzyme and a biomarker to measure a plurality of features. The floating gate may be split into two environments: a left arm (FG-L), which may be connected to the polymer channel through a solid-state electrolyte, and a right arm (FG-R), which may be capacitively connected to the controlled gate by a test fluid and may include sensor bio-recognition elements. For regular OECTs, this design constraint for efficient gating may be relaxed with the introduction of some redox reporter to raise the potential of the electrolyte and facilitate charge transfer to the polymer channel. The sensor may further comprise a third channel, termed a reference channel, that may allow for drift correction of the OECT. OECT response may be achieved using a baseline response to be compared across different biosensor platforms, the ON/OFF transistor current magnitudes are normalized to a blank: Normalized Current Response $(NCR)=|(i-i_0)/i_0|$ where i is the current difference measured from an oxidative gate voltage step in the presence of the corresponding analyte concentration and $i_0$ is this same step in the presence of no analyte for a baseline current response. This method may establish the current response from a gate voltage step in the OECT, which may be affected by the attachment of yeast cells to the gate electrode interface. The response is logarithmic with respect to analyte concentration and the slope of a log-fit correlates to the sensitivity of the specific biosensor.

Drift correction may also be provided by accounting for non-specific interactions with the sensor interfaces that cause a drift in sensor response. Response drift from physical changes to the sensor interface are inherent in biosensor systems as a function of analyte concentration, flow rate, and available binding sites. To account for this, the response from the reference channel can be subtracted in real time from the interacting peptide channel. Further, by normalizing the responses to an initial injection of bovine serum albumin (BSA) (or some other non-specific binding biomolecule used as a standard blank for non-specific adsorption) the response can mostly be attributed to that of the bio recognition element. In some embodiments, this device platform with associated controls (BSA addition, reference channel) may allow the present invention to gain a specific and amplified response to the target analyte of interest without needing to fully understand the complexity of peptide-target interaction.

The present invention features a sensor (100) for analyzing one or more features of a reaction between a first reactant and a second reactant. In some embodiments, the sensor (100) may comprise a substrate (200). The substrate (200) may comprise a reactant source (300) fluidly connected to a reactant path leading to a surface (250) of the substrate (200). The first reactant contained in the reactant source (300) may travel through the reactant path to the surface (250) to react with the second reactant to become a post-reaction mixture on the surface (250) of the substrate (200). The substrate (200) may further comprise a drain (400) fluidly connected to a drain path. The post-reaction mixture may travel from the surface (250) of the substrate (200) through the drain path to the drain (400). The sensor (100) may further comprise an electronic gate (500) in fluid communication with the post-reaction mixture for measuring the one or more features of the reaction between the first reactant and the second reactant. The one or more features may be selected from a group consisting of a rate constant of the reaction, a concentration of the first reactant in the post-reaction mixture, a concentration of the second reactant in the post-reaction mixture, and an amount of energy produced by the reaction.

The present invention features a system for analyzing two or more sets of features of a plurality of reactions between a plurality of first reactants and a second reactant. The system may comprise two or more sensors. Each sensor (100) may comprise a substrate (200). The substrate (200) may comprise a reactant source (300) fluidly connected to a reactant path leading to a surface (250) of the substrate (200). A first reactant of the plurality of first reactants contained in the reactant source (300) may travel through the reactant path to the surface (250) to react with the second reactant to become a post-reaction mixture on the surface (250) of the substrate (200). The substrate (200) may further comprise a drain (400) fluidly connected to a drain path. The post-reaction mixture may travel from the surface (250) of the substrate (200) through the drain path to the drain (400). Each sensor (100) may further comprise an electronic gate (500) in fluid communication with the post-reaction mixture for measuring a set of features of the reaction between the first reactant of the plurality of first reactants and the second reactant. One or more features of the feature set may be selected from a group consisting of a rate constant of the reaction, a concentration of the first reactant in the post-reaction mixture, a concentration of the second reactant in the post-reaction mixture, and an amount of energy produced by the reaction. The system may further comprise a computing device (600) comprising a processor capable of executing computer-readable instructions, and a memory component comprising a plurality of computer-readable instructions for accepting the two or more feature sets from the two or more sensors and analyzing the two or more feature sets.

Each sensor of the two or more sensors may be positioned in a different location from other sensors, collect the set of features at a different time from other sensors, or a combination thereof. The memory component may further comprise computer-readable instructions for executing a machine learning algorithm for analyzing the two or more sets of features. The memory component may further comprise computer-readable instructions for deriving one or more array features from the two or more sets of features selected from a group consisting of spatial distribution, distribution of rate constants, and a variety of analytes.

The present invention features a method for analyzing one or more features of a reaction between a first reactant and a second reactant. The method may comprise providing a sensor (100). The sensor (100) may comprise a substrate (200) comprising a reactant source (300). The reactant source (300) may comprise a reactant path leading to a surface (250) of the substrate (200). The first reactant contained in the reactant source (300) may travel through the reactant path to the surface (250) to react with the second reactant to become a post-reaction mixture on the surface (250) of the substrate (200). The substrate (200) may further comprise a drain (400) fluidly connected to a drain path. The post-reaction mixture may travel from the surface (250) of the substrate (200) through the drain path to the drain (400). The sensor (100) may further comprise an electronic gate (500) in fluid communication with the post-reaction mixture for measuring the one or more features of the reaction between the first reactant and the second reactant. The one or more features may be selected from a group consisting of a rate constant of the reaction, a concentration of the first reactant in the post-reaction mixture, a concentration of the second reactant in the post-reaction mixture, and an amount of energy produced by the reaction. The method may further comprise applying the second reactant to the sensor (100), and analyzing, by a computing device (600), a readout from the electronic gate (500) upon detecting the reaction between the first reactant and the second reactant.

In some embodiments, the second reactant may be derived from a biological fluid from an animal, plant, or environment, or an artificial fluid for consumption or medical purposes. The surface (250) may be accessible to the second reactant. Analyzing the one or more features may allow the sensor (100) to measure physiological parameters based on fluids produced by a human, yeast production in biofuel, or environmental parameters in a natural environment. In some embodiments, the first reactant may comprise an antibody, an aptamer, an ion gel, a protein, a peptide, a neurotransmitter, a neuropeptide, a gas molecule, a carbohydrate, a lipid, or a combination thereof, and the second reactant may comprise an antibody, an aptamer, an ion gel, a protein, a peptide, a neurotransmitter, a neuropeptide, a gas molecule, a carbohydrate, a lipid, or a combination thereof. In some embodiments, the sensor (100) may further comprise a pump for directing the first reactant from the reactant source (300) through the reactant path to the surface (250) of the substrate (200). In other embodiments, the reactant path may comprise a plurality of capillaries such that the first reactant may be directed through the reactant path by a wicking action. The plurality of capillaries may comprise a plurality of microfluidic capillaries.

In some embodiments, the sensor (100) may be communicatively coupled to a computing device (600). The computing device (600) may comprise a processor capable of executing computer-readable instructions and a memory component comprising a plurality of computer-readable instructions for implementing a machine learning algorithm for analyzing the one or more features. In some embodiments, the sensor (100) may be communicatively coupled to one or more additional sensors disposed in different locations to act as an array of sensors. The array of sensors may be capable of measuring one or more array features selected from a group consisting of spatial distribution, distribution of rate constants, and a variety of analytes. The electronic gate (500) may be disposed above, lateral to, behind, or in front of the surface (250) of the substrate (200). In some embodiments, the sensor (100) may further comprise an attachment component allowing the sensor (100) to attach to a surface or tissue. The surface or tissue may be an animal surface, an animal tissue, a synthetic surface, or a natural surface. The natural surface may be soil, a plant, or any surface that may be found in nature.

In some embodiments, the sensor (100) may further comprise an electrolyte disposed between the electronic gate (500) and the substrate (200). The electrolyte may comprise a redox-based modifier having a reduction (oxidation) potential that may be energetically equivalent to the substrate (200). A surface of the electronic gate (500) may comprise an oxidation or reduction element. The substrate may comprise a solid-state printable material. The sensor (100) may further comprise an interacting channel comprising a first control gate electrode and a first solid-state analyte disposed in a first biofluid for providing a charge transfer to the electronic gate (500). The sensor (100) may further comprise a reference channel comprising a second control gate electrode and a second solid-state analyte identical to the first solid-state analyte disposed in a second biofluid identical to the first biofluid to allow for drift correction of an output of the sensor (100). The substrate (200) may further comprise of a conductive polymer such as poly(3-hexylthiophene) (P3HT) and poly[2-5-bis(3-dode-cylthi-ophen-2-yl)thieno[3,2-b ]thiophene)] (PBTTT-C12). Note that the substrate may comprise a wide variety of additional or differing polymers from the given examples. The sensor (100) may implement a Marcus-Gerischer perspective for reactions at the electronic gate (500). The sensor (100) may be low powered or self-powered.

EXAMPLE 1

The following is a non-limiting example of the present invention. It is to be understood that said example is not intended to limit the present invention in any way. Equivalents or substitutes are within the scope of the present invention.

There are two main modes of OECT operation in a sensing configuration, focusing on a prototypical mode channel and the generalized description of a gate electrode. In the non-faradaic or capacitive mode, the gate electrode is assumed to act like an ideal polarizable electrode, characterized as a capacitor due to charge separation at the electrode/electrolyte interface. This scenario represents a simplified application of OECT-based biosensors, whereby biomarkers bind with a surface-adsorbed bio-recognition element (BRE), systematically altering the gate capacitance as a function of coverage. The observed change in gate/

BRE/biomarker interface capacitive behavior can be highly dependent on the gate electrode material of choice, ionic strength, and solvent effects, and in the case of biofluids, electrode fouling effects. Challenges in capacitive modes include only small changes with binding (typically <5%), strong dependence of Debye length, and overall, monolayer-like structures on gate electrodes only exhibit a capacitance of 1-10 μF/cm2. Thus, a gate electrode would need to be on an order of 1 cm2 to have the same capacitance as the semiconductor channel with a volume of 1 mm3.

For a p-type channel, a redox-active species is sensed at a negatively charged gate electrode when the oxidized form ($O_{gate}$) is reduced ($R_{gate}$). Critically, the flow of electrons through the circuit efficiently reduces the interfacial potential drop at the gate, with a substantial increase in the gate current ($I_g$) and electrolyte potential $\phi^E$. The combined effect is an enhancement to the channel conductivity through increased carrier density, relative to the capacitive mode at the same gate voltage ($V_g$). Double-layer structures at the gate are drawn in detail with pictorial representation showing solvated ions in the supporting electrolyte and redox-active species.

In some embodiments, the gate electrodes may comprise a non-metal material. In other embodiments, the gate electrodes may comprise a metal material. In some embodiments, the device may comprise a p-type polymer, an n-type polymer, or a combination thereof. In some embodiments, the present invention implements an accumulation mode channel. In other embodiments, the present invention implements a depletion mode channel.

The potential difference between the gate and channel ($V_g$) is distributed across the gate/electrolyte and channel/electrolyte interfaces. A reference electrolyte potential ($\phi^E$) is qualitatively shown for the two modes. In the faradaic mode, the potential drop at the gate/electrolyte interface is small, which allows a larger potential drop at the channel/electrolyte interface. Most critically, $\phi^E$ in the faradaic mode is comparably higher than that in the capacitive mode. In other words, $\phi^E$ is a variable that interconnects the electrochemical process at the gate and the doping process in the channel.

Briefly, any change in the redox-active species at the gate electrode (i.e., change in the biomarker concentration) changes the chemical potential, resulting in a shift in electrolyte potential $\phi^E$ via equation 1:

$$\phi^E = \frac{V_g}{1+r} + E^{0\prime} + \frac{RT}{nF}\ln\frac{C_O}{C_R} \tag{1}$$

where n is the number of electrons transferred and $C_O$ and $C_R$ are the concentrations of oxidized and reduced species at the gate electrode, respectively. In eq 1, a constant capacitance ratio between the channel and gate is assumed ($\gamma=C_c/C_g$, where $C_c$ and $C_g$ are the channel and gate capacitances, respectively). However, a simple Nernst approximation causes a number of fundamental interpretation challenges including the following: (i) the Nernst potential is an equilibrium expression routed in thermodynamics, whereas the OECT is operated in a transient and/or steady-state mode (under transport and non-equilibrium considerations), (ii) the concentration ratios of redox species at the gate electrode cannot be directly resolved, and (iii) the channel capacitance is highly dependent on the semiconductor of choice, film geometry (thickness, width, and length), solvent and electrolyte effects, electrochemical potential, and modulation frequency. To the last point, the channel is not a pure capacitance element but rather a complex potential-dependent circuit that includes multiple resistive and constant phase elements. Collectively, the electrolyte potential (pE that dictates the device response is determined by the sophisticated balance between both the electrochemical processes at the gate and channel.

The overlap in the polymeric DOS of the channel with the DOS of the electrolyte undergoing charge transfer at the gate electrode is a key design parameter in OECTs. The complexity and redox properties of materials can be highly dependent on electrolyte conditions; the present invention implements only highly characterized, simple molecular redox probes with different standard reduction potentials as a proof-of-concept. While many bioelectronic devices target aqueous environments for sensing, quantifying the absolute electrochemical potentials in the absence of other redox interferences is of utmost importance. OECT characterizations in dry acetonitrile (MeCN) were observed to avoid parasitic faradaic pathways such as oxygen and water reduction at the gate and/or interference with the polymer channel. Additionally, the use of MeCN eliminated possible proton-coupled electron transfer reaction pathways that are well established to shift the reduction potential of redox moieties and/or cause undesired evolution of new chemical species. Lastly, MeCN affords the use of organic electrolytes, which are non-coordinating, unlike halide-based salts used in aqueous systems.

The Marcus-Gerischer model describes heterogeneous charge transfer between a solid-state electrode and a solvated redox probe using an effective electronic distribution function of solvation states for a prototypical oxidized ($W_{ox}(E)$, unoccupied levels) and reduced ($W_{red}(E)$, occupied levels) species:

$$W_{ox}(E) = W^0 \exp\left[-\frac{\left(E - E_{F,redox}^0 + \lambda\right)^2}{4kT\lambda}\right]; \tag{2}$$

$$W_{ox}(E) = W^0 \exp\left[-\frac{\left(E - E_{F,redox}^0 - \lambda\right)^2}{4kT\lambda}\right] \tag{3}$$

where $\lambda$ is the reorganization energy (assuming $\lambda_{ox}=\lambda_{red}=\lambda$), k is Boltzmann constant, T is temperature, E is the electronic energy, and $$E_{F,redox}^0$$

is the standard Fermi level of a redox system. The pre-exponential factor ($W^0=(4\ kT\lambda)^{-1/2}$) is a normalizing constant to make the integrated probability unity ($\int W(E)dE=1$). The density of electronic states is proportional to the concentration of the reduced (cred) and oxidized (cox) species, where the total distributions are:

$$D_{ox}(E)=c_{ox}W_{ox}(E);\ D_{red}(E)=c_{red}W_{red}(E) \tag{4}.$$

Compared to an equal ratio, an excess mole fraction of oxidized species has more unoccupied states at the same electronic energy level when the total concentration is kept constant. All values are calculated from cyclic voltammetry (CV) using a standard platinum electrode and are in agreement with the reported literature and values. For clarity, values are referenced versus the vacuum scale, under the assumption that 0 V versus the Ag/Ag$^+$ reference electrode corresponds to −4.87 eV versus vacuum level.

According to Equation (2) and (4), the total distribution of DOS for solvated oxidized species is $$D_{ox}(E) = c_{ox}W_{ox}(E) = c_{ox}W^0 \exp\left[-\frac{\left(E - E_{F,redox}^0 + \lambda\right)^2}{4kT\lambda}\right] \tag{S1}$$

where $\lambda$ is the reorganization energy (assuming $\lambda_{ox}=\lambda_{red}=\lambda$), k is Boltzmann constant, T is temperature, $W_{ox}(E)$ is the distribution function, E is the electronic energy, and $$E_{F,redox}^0$$

is the standard Fermi level of a redox system.

The pre-exponential factor ($W^0=(4\ kT)^{-1/2}$) is a normalizing constant to make the integrated probability unity ($\int W(E)dE=1$). It is noted that the density of electronic states is proportional to the concentration of the reduced (cred) and oxidized (cox) species in the electrolyte. In a prototypical OECT with p-type accumulation mode channel working in the faradaic mode, a reduction process happens at the gate electrode and electron transfer takes place from the occupied states on the electrode to the unoccupied states on the oxidized species with matched energy. The density of occupied electronic states on the electrode is given by f(E)p(E), where p(E) is the distribution of energy state in the electrode, and f(E) is the Fermi function representing the probability that a state of energy E is occupied by an electron. Then the current density of the faradaic process at the gate is given by the Marcus-Gerischer equation:

$$J_{Gate} = e\kappa \int_{-\infty}^{E_F} D_{ox}(E)f(E)p(E)dE = e\kappa c_{ox}\int_{-\infty}^{E_F}$$

$$f(E)p(E) \exp\left[-\frac{\left(E - E_{F,redox}^0 + \lambda\right)^2}{4kT\lambda}\right] \tag{S2}$$

where $\kappa$ is a transmission coefficient ranging between 0 and 1, and Z is the frequency of the reaction coordinate. EF is the Fermi level of the gate electrode. The pre-exponential factor $\bar{k}$ describes the interaction between the electrode and redox system and the normalization factor that includes $\kappa$, Z, and $W^0$. By applying a negative voltage on a typical metal gate electrode, EF moves upward towards high energy. A much enhanced electron transfer kinetics is thus achieved by having more energetic overlap between corresponding states on both sides.

In most cases, the overlap between energy states on both interfaces is limited to a rather small energy range (within ~1 kT around $E_F$) since the distribution function $W_{ox}(E)$ varies exponentially with $E^2$. The integral Equation S2 can be approximated by inserting dE=1 kT and E=$E_F$:

$$J_{Gate} = e\kappa Z\left(\frac{kT}{\pi\lambda}\right)^{1/2} c_{ox} \exp\left[-\frac{\left(E - E_{F,redox}^0 + \lambda\right)^2}{4kT\lambda}\right] \tag{S3}$$

which is mathematically identical to the equation for electron transfer modeled by the Marcus theory. Additionally, $$E_F - E_{F,redox}^0$$

can be written in terms of overpotential in volt $$\left(\eta = \frac{E_F - E_{F,redox}^0}{e}\right)$$

at the gate using $$E_{F,redox}\left(E_{F,redox} = kT \ln \frac{c_{ox}}{c_{red}} + E_{F,redox}^0\right),$$

the actual Fermi level of the redox systems. S3 then becomes:

$$J_{Gate} = e\kappa Z\left(\frac{kT}{\pi\lambda}\right)^{1/2} c_{ox} \exp\left[-\frac{\left(e\eta + E_{F,redox} - E_{F,redox}^0 + \lambda\right)^2}{4kT\lambda}\right]. \quad (S4)$$

By the introduction of empirical transfer factor $\alpha$, Equation S4 can also be written as:

$$J_{Gate} = k_0^- c_{ox} \exp\left[-\frac{(e\eta + \lambda)^2}{4kT\lambda}\right] \quad (S5)$$

$$\text{where } k_0^- = k_0 \exp\left(\frac{(1-\alpha)(E_F - E_{F,redox})}{kT}\right),$$

$k_0$ is the rate constant in the equilibrium under standard condition. The Butler-Volmer expression can be then derived from Equation S5 because of the similarity of its transition state model to the parabolic energy surface profile as a harmonic oscillator for the Marcus theory:

$$J_{Gate} = -j_0 e^{-\frac{\alpha e\eta}{kT}} = k_0 c_{ox}^{1-\alpha} c_{red}^\alpha e^{-\frac{\alpha e\eta}{kT}} \quad (S6)$$

where $j_0$ is the exchange currently density when the net current is zero at equlibrium, and $$j_0 = k_0 c_{ox} \exp\left(-\frac{\alpha\left(E_F - E_{F,redox}^0\right)}{kT}\right) = k_0 c_{ox}^{1-\alpha} c_{red}^\alpha.$$

A similar series of current density expressions can be derived for the oxidation process at the gate but herein is ignored.

Regarding polymer choice for the semiconductor channel, there are a number of high-transconductance options. As a sensor should have a low "off" current and based on the redox probes used, the present invention may implement p-type accumulation mode approaches. The present invention may employ regioregular poly(3-hexylthiophene) (rr-P3HT), as it is of low cost and readily available in large quantities in the organic electronics community. These two factors are critical for biological studies, which require a large number of devices. Furthermore, rr-P3HT is considered the prototypical organic electronic material and as such, the electrochemical properties have been highly characterized. The oxidation potential is such that a number of small molecules, common redox probes, can be utilized with systematic variation in the formal potential. The present invention may implement a second polymer, PBTTT-C12, which exhibits a greater degree of structural ordering and orientation, resulting in a higher carrier mobility and volumetric capacitance compared to P3HT in electrolyte. The estimation of the DOS for organic semiconducting polymers has been previously described.

The density of electrochemically active states for conductive polymers can be derived from cyclic voltammetry. Briefly, the current density (J) of the polymer under a potential scan can be described as $J_{Polymer}=-vdC_\mu$ (S7) where v is the potential scan rate, d is the film thickness and $C_\mu$ is the volumetric capacitance, which accounts for changes in electrochemically active states due to different electrolyte environments, including both solvation and ion intercalation effects. Thus, the volumetric capacitance is proportional to the carrier density $(d_p/d_E)$ under the assumption of the majority of the observed current is faradaic via $$C_\mu = e^2 \frac{d_p}{dE_{Polymer}} = e^2 DOS(E_{Polymer}) \quad (S8)$$

where e is the elementary charge and $DOS(E_{Polymer})$ is the energy-dependent density of states of the polymer. From Equation (S7) and (S8), the current density of the polymer $(J_{Polymer})$ can be written as $J_{Polymer}=e^2 vdDOS(E_{Polymer})$ (S9).

Sufficient $V_g$ is defined by the energy offset of $O_{gate}$ and $R_{polymer}$, which can be approximately estimated from the difference between $E^0$ ' of the redox probe and oxidation potential of the polymer. For example, the process $F_4TCNQ+e^-\rightarrow F_4TCNQ^{\bullet-}$ (5) would occur at a lower magnitude $V_g$ than the process $TCNQ+e^-\rightarrow TCNQ_{\bullet-}$ (6) due to the differences between $TCNQ/TCNQ^{\bullet-}$ (−4.77 eV or −0.10 V) and $F_4TCNQ/F_4TCNQ^{\bullet-}$ (−5.13 eV or 0.26 V) relative to the oxidation potential of the polymer. This hypothesis in a DOS perspective indicates that the behavior of the OECT extends beyond changing the reduction potential of the molecule at the gate electrode.

Considering operation near a zero applied source-drain voltage with fluxes at both the polymer and the gate, the channel can thus be assumed grounded for mathematical simplification. In this case, the electrochemical doping of the channel is fully coupled with the faradaic process at the gate, and the current flowing across the polymer channel/electrolyte interface should equal to the gate current in the absence of any parasitic pathways. Herein Equations S9 and S2 (as well as its derivations S3 and S4) are correlated as $J_{Polymer}A_{Polymer}=J_{Gate}A_{Gate}$ (S10).

$$\text{Thus, } e^2 A_{Polymer} vdDOS(E_{Polymer}) = e\kappa Z \int_{-\infty}^{E_F} D_{ox}(E)f(E)p(E)dE = \quad (S11)$$

$$e A_{Gate} k c_o \int_{-\infty}^{E_F} f(E)p(E) \exp\left[-\left(-\frac{\left(E - E_{F,redox}^0 - \lambda\right)^2}{4kT\lambda}\right)\right]dE$$

$$= e A_{Gate}\kappa Z\left(\frac{kT}{\pi\lambda}\right)^{1/2} c_{ox} \exp\left[-\frac{\left(e\eta + E_{F,redox} - E_{F,redox}^0 + \lambda\right)^2}{4kT\lambda}\right].$$

Here the processes at both gate and the polymer channel are developed and correlated based on both intrinsic material parameters and external parameters covering the selection and engineering of channel, redox species, electrolyte environment and voltage applied. It helps to disclose how these two interfaces interplay dynamically to determine the OECT performance in the faradaic mode. To name a few, the gate current should increase with more oxidized (reduced) species by having a larger cox (or crew in the case of reduction) This leads to a heavier doping of the polymer channel and therefore a higher drain current, making it appropriate for a sensor platform. By shifting the DOS distribution of the oxidized species ($D_{ox}(E)$) closer to the polymer (DOS(E-$_{Polymer}$)), it will allow a larger current to flow across both interfaces at a smaller $V_g$. A more negative $V_g$ leads to a higher $E_F$ that can maximize the integral on the right with more overlap between the corresponding energy states on the gate and oxidized species, contributing to an enhanced faradaic current flux as also described by the overpotential η.

Equation S4 introduces an overpotential η that represents the potential drop at the gate/electrolyte interface. $E_{polymer}$ can also be treated as the electrochemical potential of the polymer versus the electrolyte potential as referred in a three-electrode system where the working electrode is grounded. In the OECT system, $\phi^E$ is the electrolyte potential versus the polymer channel which can be treated as grounded here. As a result $DOS(E_{Polymer})=DOS'(-e\phi^E)$ (S12). The applied gate voltage $V_g$ drops separately at the gate/electrolyte and channel/electrolyte interfaces (assuming the channel is grounded). $V_g=\eta+\phi^E$ (S13) Thus, Equation S11 becomes $$e^2 A_{Polymer} v dDOS'(-e\varphi^E) =$$
$$eA_{gate}\kappa Z(kT)^{1/2}c_{ox} \exp\left[-\frac{\left(e(V_g-\phi^E)+E_{F,redox}-E^0_{F,redox}+\lambda\right)^2}{4kT\lambda}\right]. \quad (S14)$$

From Equation S14, all the other energy terms are reduced down to known values such as $V_g$ and $$E^0_{F,redox},$$

and the electrolyte potential $\phi^E$ determines the DOS of the polymer on the left as well as the current flux on the right. The two processes at the gate and channel interfaces are clearly interconnected by $\phi^E$ that is a measurable variable. The usefulness of the Marcus-Gerischer perspective is validated by the measurement of $\phi^E$ during the OECT operation.

Voltage can be reduced by aligning DOS of the polymer with the electrolyte. This is validated by first utilizing the device with a P3HT polymer channel and introducing TCNQ, $F_4$TCNQ, and $Fc^+$ as the oxidized species into the electrolyte at the same concentration of 100 μM.

The MeCN control shows a low source-drain current ($I_d$) and only a small increase in gm with increasing gate voltage, indicative of a predominant capacitive gate electrode effect. The addition of oxidants to the electrolyte significantly enhances $I_d$, consistent with the faradaic mode operation. All three redox-containing electrolytes demonstrate a $V_g$-dependent $I_d$ that maximizes at ~1.3 mA, indicating complete electrochemical doping of the channel. Their gm plots all exhibit triangular shapes as a function of Vg with similar maximum $g_m$ values ($g_{m,max}$) between 2.5 and 2.8 mS.

As hypothesized, the transfer curve of P3HT devices shifts systematically with respect to redox potentials of the electrolyte. Specifically, Id exceeds 1 mA at $V_g$ around −0.4 V for $F_4$TCNQ, −0.6 V for $Fc^+$, and −0.8 V for TCNQ. A systematic shift in $V_g$ associated with $g_{m,max}$ is observed in accordance with the standard reduction potential of the redox probe relative to the DOS of the polymer. Briefly, the replacement from TCNQ to $Fc^+$ changes the peak position from −0.6 to −0.4 V, and $F_4$TCNQ has a peak value appearing as low as −0.2 V. Introduction of reductant species, such as Fc and TPD (N,N'-bis(3-methylphenyl)-N, N'-diphenylbenzidine), does not show any discernible change compared to MeCN control and the device still operates in the capacitive mode. In a Marcus-Gericher perspective, this is rationalized in that there are no available states in the electrolyte to accept an electron from the negatively polarized metal gate.

The appropriate working range is negatively shifted from $F_4$TCNQ to TCNQ according to the E0' difference. The MeCN control, denoted by the asterisk, is always below the threshold value. It is worth noting the transconductance plot also bears a dependence on the drain voltage. In addition to the increase in $I_d$, the $V_g$ working range for each species shifts negatively, as observed when comparing a Vd of −0.3 to −0.7 V. This is interpreted as an increase in $V_d$, which reduces the potential difference between the gate and channel, thus lowering the kinetics of the faradaic reaction at the gate with a decrease in $\phi$E, and thus the electrochemical doping in the channel. Therefore, for sensing, one strategy to reduce power consumption is to configure the device such that the lower necessary Vg is achieved at the lowest possible $V_d$.

Thus, a higher $g_{m,max}$ can be achieved via a large W/L ratio or increased thickness yet with the requirement of a larger gate voltage. The shift of $\phi$E to a lower magnitude (by $V_d$ or the channel capacitance increase) demands a higher Vg to reach gm,max. Any electrochemical event (capacitance, charge transfer, concentration ratios, etc.) that shifts $\phi$E to a higher magnitude thus lowers necessary $V_g$. For example, in sensing, increasing the concentration of the redox molecule at the gate yields a lower $V_g$ for $g_{m,max}$ as well as a higher $g_{m,max}$ value (i.e., sensing higher concentrations lowers power requirements).

The $F_4$TCNQ device warrants special attention, as $F_4$TCNQ is an established dopant for P3HT with dynamically changing charge transfer states. The density of states overlap between redox molecules and polymers is the driving force for charge transfer. The role of electrolyte doping, contextualized to an OECT and the DOS model, can be interpreted as $F_4$TCNQ having an effective distribution of energy states that overlaps with the DOS of rr-P3HT. This can induce the doping process spontaneously (i.e., the net free-energy change is negative), yielding P3HT+ and $F_4$TCNQ− and thus an increase in conductivity of the polymer.

It is noted that when $V_g$=0 V, the OECT interfaced with the $F_4$TCNQ electrolyte has an $I_d$≈0.1 mA and a gm value of ~1 mS, higher than any value achieved for the MeCN control. This behavior is analogous to a two-electrode system consisting of a polymer electrode and a metal electrode, which works as an amperometric OECT. This chemical doping of the polymer by the electrolyte is more apparent for the device made from PBTTT using $F_4$TCNQ, where there is a greater degree of DOS overlap between the polymer and electrolyte, leading to a larger gm value of ~2.3 mS at zero $V_g$.

There is no overlap in the density of states between P3HT and the TCNQ oxidant (species to be reduced), which indicates that chemical doping is not thermodynamically possible, consistent with prior studies. Additional validation of the feasibility of possible charge transfer in the electrolyte system (i.e., under electric fields in the OECT) is done using CV of P3HT (on ITO substrates) in the MeCN control electrolyte and with 100 μM of TCNQ and $F_4$TCNQ. Charge transfer to TCNQ is not spontaneous but only occurs upon driving the electrochemical potential. Specifically, a redox feature for TCNQ is not observed within the P3HT doping potential region (anodic of 0.1 V vs Ag/Ag+) and no additional current in this region above the MeCN control. Rather, the oxidation/reduction of TCNQ occurs cathodic of 0V vs Ag/Ag+. The lack of an additional redox peak, i.e., direct overlap of the voltammogram with the MeCN control in the polymer doping region, confirms that the DOS picture accurately predicts that chemical doping of P3HT by TCNQ is forbidden.

Alternatively, experimentation shows reversible $F_4$TCNQ oxidation/reduction peaks within the P3HT doping region at +0.36 V (−5.23 eV) and +0.30 V (−5.17 eV), as predicted by the DOS overlap. The second redox feature of $F_4$TCNQ at a more negative potential is the subsequent reduction of $F_4$TCNQ− to $F_4$TCNQ$^{2-}$, which does not participate in P3HT doping. Such a small change in current detected by cyclic voltammetry can yield a significant change in Id and gm, strongly suggesting the approach of efficiently improving the OECT performance by the introduction of appropriate redox molecules (dopants).

However, while the spontaneous doping of the channel increases the transconductance at a $V_g$=0 V, this doping effect comes with some disadvantages. In the case of biosensing, the presence of a chemical doping species would result in a higher "OFF" current, analogous to PEDOT:PSS-based OECTs. In addition to the chemical doping, applying a negative $V_g$ value in the OECT device with $F_4$TCNQ will increase $I_d$ by further reducing the oxidant at the gate and oxidizing more Rpolymer in the channel for doping. A gate voltage more negative beyond −0.7 V did not further increase $I_d$ yet accelerated polymer degradation as evident in a loss of channel conductivity from over-oxidation, a phenomenon also observed when using a higher concentration of $F_4$TCNQ. In some cases, a slightly higher $V_g$ but with no chemical doping of the channel could be a preferred architecture, i.e., the Fc+ or TCNQ-based devices.

As mentioned previously, $\phi^E$ interconnects the electrochemical processes at the gate and channel. Therefore, accuracy is in-depth verified by monitoring the change in $\phi^E$ during the OECT operation. Simultaneous measurement of electrolyte potential is achieved with a slight modification to the OECT characterization approach. The setup is analogous to a cyclic voltammogram at the gate electrode of an operating OECT and provides a simultaneous measurement of $\phi^E$ by the use of a reference electrode (i.e., Ag/Ag+) and a multimeter. It allows determination of the exact real-time $\phi^E$ as a function of applied gate voltage while measuring $I_g$ and $I_d$ at the same time in response to the MeCN control, TCNQ, and $F_4$TCNQ.

The low $I_g$ and square-like feature cathodic of −0.4 V for the MeCN control are associated with capacitive double-layer charging. Large current responses are shown for TCNQ and $F_4$TCNQ with readily visible reduction peaks (negative current) at around −0.8 V (TCNQ) and −0.4 V ($F_4$TCNQ), in agreement with their offset in peak DOS between the oxidant and polymer. This OECT cyclic voltammogram couples the gate process with the electrochemical process at the polymer channel like a two-electrode system, and thus oxidation peaks in the reverse scan are not well resolved.

Consistent results are obtained for $I_g$ and $I_d$, validating the authenticity to investigate and interpret the standard OECT operation using the experimental setup. The results clearly indicate that the channel conductivity (or $I_d$) does not follow a linear relationship versus electrolyte potential, consistent with a voltage-dependent change in carrier density. This counters prior efforts to model OECT channels as simple capacitive elements and illustrates the need to account for the complex voltage-dependent behaviors associated with pseudocapacitance of organic semiconducting polymers and the variances that occur as a function of electrolyte composition (solvents, supporting electrolytes, and/or redox species).

The MeCN control shows a gradual increase in the magnitude of $\phi^{9E}$ with a negative sweep in $V_g$. The introduction of TCNQ reduces the potential drop at the gate interface by moving into the faradaic mode, causing a downward shift in $\phi^E$. It allows more $R_{polymer}$ to be oxidized with a commitment increase in $I_d$, as illustrated by its early onset at $V_{g=}$0.3 V and a much larger maximum value about −210 μA at $V_g$=−0.8 V than about −30 μA of the MeCN control. This trend is in accordance with the proposed Marcus-Gerischer perspective in which the presence of an oxidant initiates faradaic current at the gate and drives the electrochemical potential of the polymer ($E_{Polymer}$) to a higher level as demonstrated by $\phi^E$. A significantly enhanced Id is thus observed by the strong doping of the polymer from this faradaic process.

$F_4$TCNQ, distinctly, has an initial $\phi^E$ of −0.35 V and Id about −30 μA before $V_g$ sweep, which match well with previous results of non-zero $g_m$ and $I_d$ at $V_g$=0 V, again verifying the chemical doping. The initial $\phi^E$ in essence represents the open circuit potential (OCP) of the electrolyte system, which corresponds to $E_{F,redox}$ or the so-called chemical potential determined by the redox molecules and relative concentration ratio. The change from TCNQ to $F_4$TCNQ shifts EFermi, redox and so as the DOS of the electrolyte to an energy level overlapped with the P3HT polymer and enables spontaneous electrochemical processes at the channel and gate in the absence of $V_g$. The redox processes lead to larger $I_g$ and an always higher $\phi$E from the start of $V_g$ sweep. The initial spontaneous doping and larger faradaic current flow well explain the apparent $I_d$ difference between these two probes. Though the magnitude of $I_g$ and $\phi^E$ are always higher, $I_d$ for TCNQ reaches the same maximum as $I_d$ for $F_4$TCNQ at around −0.8 V. When $V_g$ is more negative, there is still an increase in $\phi^E$ for both species; however, $I_d$ keeps relatively constant and then decreases afterward, consistent with over-oxidation of the channel previously described.

In summary, the measurement of electrolyte potential and simultaneous investigation of gate and drain currents using the modified setup have successfully addressed the dynamic change of the OECT under operation and disclosed how each interface behaves and interacts reciprocally. By changing the redox probe or material of the polymer channel, the initial energetic overlap between DOS of the electrolyte and channel varies systematically, leading to a difference in the magnitude of $I_g$ as demonstrated in our Marcus-Gerischer perspective. The conductivity of the channel, represented by $I_d$, is then the accumulated contribution from continuous $I_g$ that gradually dopes the channel during the operation. The accurate prediction of Id requires the relationship of carrier mobility as a function of doping level, which can be derived electrochemically. The electrochemical potential of the polymer channel and its effective DOS, which is energy-dependent, are changed accordingly as measured in $\phi^E$. In other words, $\phi^E$ determines the doping level of the channel. Since the gate faradaic process is determined by its over-potential $\eta$, which equals to $V_g - \phi^E$, $\phi_E$ interconnects both processes at interfaces and can be used to explain the OECT performance.

The introduction of the Marcus-Gerischer perspective helps to view the OECT device from the DOS perspective in kinetics consideration using a modified two-electrode system analogy and overcomes the limitations in the equilibrium Nernst approximation. Not only for the metal gate, the DOS argument makes it valid to also apply to the OECT using a semiconductor gate electrode, which extends its versatility and practicability. Their relationship is built up by incorporating other necessary kinetic parameters ($\lambda$, $$E^0_{F,redox},$$

etc.) for the gate process and channel engineering factors such as its geometry and DOS of the polymer. The latter is rather an empirical parameter that depends on material selection, processing, and environment and can be instead practically derived from experimental measurements. The use of a redox molecule with increased DOS overlap to the polymer can significantly decrease the gate voltage required to drive the device and improve its power efficiency. An increase in the DOS of the polymer (such as from the selection of the processing strategy, ion, and solvent) or a larger surface area/thickness of the channel ensures the capacity for a higher $I_g$ to flow across the channel/electrolyte interface with more charge accumulation for electrochemical doping. Simultaneously, it often comes with a larger Id initially, which yields a background current in the OFF state.

Although there has been shown and described the pre-ferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:
1. A sensor for analyzing one or more features of a reaction between a first reactant and a second reactant, the sensor comprising:

a. a substrate, the substrate comprising:
  i. a reactant source fluidly connected to a reactant path leading to a surface (250) of the substrate, wherein the first reactant contained in the reactant source travels through the reactant path to the surface to react with the second reactant to become a post-reaction mixture on the surface of the substrate,
  ii. a drain fluidly connected to a drain path, wherein the post-reaction mixture travels from the surface of the substrate through the drain path to the drain; and
b. an electronic gate in fluid communication with the post-reaction mixture for measuring the one or more features of the reaction between the first reactant and the second reactant;
  wherein the one or more features are selected from a group consisting of a rate constant of the reaction, a concentration of the first reactant in the post-reaction mixture, a concentration of the second reactant in the post-reaction mixture, and an amount of energy produced by the reaction.

2. The sensor of claim 1, wherein analyzing the one or more features allows the sensor to measure physiological parameters of fluids produced by an animal.

3. The sensor of claim 1 further comprising a pump for directing the first reactant from the reactant source through the reactant path to the surface of the substrate.

4. The sensor of claim 1, wherein the reactant path comprises a plurality of capillaries, wherein the first reactant is directed through the reactant path by a wicking action.

5. The sensor of claim 1, wherein the sensor is communicatively coupled to a computing device.

6. The sensor of claim 5, wherein the computing device implements a machine learning algorithm for analyzing the one or more features.

7. The sensor of claim 1, wherein the sensor is communicatively coupled to one or more additional sensors disposed in different locations to act as an array of sensors.

8. The sensor of claim 7, wherein the array of sensors are capable of measuring one or more array features selected from a group consisting of spatial distribution, distribution of rate constants, and a variety of analytes.

9. The sensor of claim 1 further comprising an attachment component allowing the sensor to attach to a surface or tissue.

10. The sensor of claim 1 further comprising an interacting channel comprising a first control gate electrode and a first solid-state analyte disposed in a first biofluid for providing a charge transfer to the electronic gate.

11. A method for analyzing one or more features of a reaction between a first reactant and a second reactant, the method comprising:
a. providing a sensor, wherein the sensor comprises:
  i. a substrate, the substrate comprising:
    A. a reactant source fluidly connected to a reactant path leading to a surface of the substrate, wherein the first reactant contained in the reactant source travels through the reactant path to the surface to react with the second reactant to become a post-reaction mixture on the surface of the substrate,
    B. a drain fluidly connected to a drain path, wherein the post-reaction mixture travels from the surface of the substrate through the drain path to the drain; and
  ii. an electronic gate in fluid communication with the post-reaction mixture for measuring the one or more features of the reaction between the first reactant and the second reactant;

wherein the one or more features are selected from a group consisting of a rate constant of the reaction, a concentration of the first reactant in the post-reaction mixture, a concentration of the second reactant in the post-reaction mixture, and an amount of energy produced by the reaction;

b. applying the second reactant to the sensor; and c. analyzing, by a computing device, a readout from the electronic gate upon detecting the reaction between the first reactant and the second reactant.

12. The method of claim 11, wherein analyzing the one or more features allows the sensor to measure physiological parameters of a fluid produced by an animal.

13. The method of claim 11, wherein the sensor (100) further comprises a pump for directing the first reactant from the reactant source (300) through the reactant path to the surface (250) of the substrate (200).

14. The method of claim 11, wherein the reactant path comprises a plurality of capillaries, wherein the first reactant is directed through the reactant path by a wicking action.

15. The method of claim 14, wherein the plurality of capillaries comprises a plurality of microfluidic capillaries.

16. The method of claim 11, wherein the computing device implements a machine learning algorithm for analyzing the one or more features.

17. The method of claim 11, wherein the sensor is communicatively coupled to one or more additional sensors disposed in different locations to act as an array of sensors.

18. The method of claim 17, wherein the array of sensors are capable of measuring one or more array features selected from a group consisting of spatial distribution, distribution of rate constants, and a variety of analytes.

19. The method of claim 11, wherein the sensor further comprises an attachment component allowing the sensor to attach to a surface or tissue.

20. The method of claim 11, wherein the sensor wherein the surface or tissue is an animal surface, an animal tissue, a synthetic surface, or a natural surface.

\* \* \* \* \*